(12) United States Patent
Iida et al.

(10) Patent No.: US 12,285,548 B2
(45) Date of Patent: Apr. 29, 2025

(54) INFORMATION PROCESSING APPARATUS AND INFORMATION PROCESSING METHOD

(71) Applicant: SONY GROUP CORPORATION, Tokyo (JP)

(72) Inventors: Fumihiko Iida, Tokyo (JP); Yousuke Kawana, Tokyo (JP); Yu Aoki, Tokyo (JP); Kentaro Ida, Tokyo (JP); Satoshi Nakamaru, Tokyo (JP); Itiro Siio, Tokyo (JP); Momoko Iwami, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 943 days.

(21) Appl. No.: 17/288,865

(22) PCT Filed: Sep. 9, 2019

(86) PCT No.: PCT/JP2019/035353
§ 371 (c)(1),
(2) Date: Apr. 26, 2021

(87) PCT Pub. No.: WO2020/095530
PCT Pub. Date: May 14, 2020

(65) Prior Publication Data
US 2022/0001065 A1 Jan. 6, 2022

(30) Foreign Application Priority Data
Nov. 6, 2018 (JP) ................................ 2018-208706

(51) Int. Cl.
*A61L 9/12* (2006.01)
*A61L 9/14* (2006.01)

(52) U.S. Cl.
CPC ................. *A61L 9/125* (2013.01); *A61L 9/14* (2013.01); *A61L 2209/111* (2013.01); *A61L 2209/133* (2013.01)

(58) Field of Classification Search
CPC ...... A61L 9/125; A61L 9/14; A61L 2209/111; A61L 2209/11
See application file for complete search history.

(56) References Cited

U.S. PATENT DOCUMENTS

| 2010/0205753 A1* | 8/2010 | Kim ...................... D06F 39/083 |
| | | 68/200 |
| 2015/0083817 A1* | 3/2015 | Kim ...................... G06F 3/0416 |
| | | 239/289 |

(Continued)

FOREIGN PATENT DOCUMENTS

| JP | 2002-369872 A | 12/2002 |
| JP | 2004-081851 A | 3/2004 |

(Continued)

OTHER PUBLICATIONS

International Search Report and Written Opinion of PCT Application No. PCT/JP2019/035353, issued on Oct. 8, 2019, 09 pages of ISRWO.

*Primary Examiner* — Mohammad Ali
*Assistant Examiner* — Vincent W Chang
(74) *Attorney, Agent, or Firm* — CHIP LAW GROUP

(57) ABSTRACT

An information processing apparatus includes an input unit and a control unit. Sensing information sensed in a predetermined space is input into the input unit. The control unit controls, in accordance with a result obtained by analyzing states or attributes of a plurality of users existing in the space on a basis of the sensing information, output of a scent from the scent output apparatus to each of the users for each user.

13 Claims, 12 Drawing Sheets

(56) References Cited

U.S. PATENT DOCUMENTS

| | | | |
|---|---|---|---|
| 2016/0022854 A1* | 1/2016 | Shah | A61L 2/24 |
| | | | 392/386 |
| 2016/0231720 A1* | 8/2016 | Choi | A61L 9/125 |
| 2017/0061475 A1* | 3/2017 | Kuwabara | G06Q 30/02 |
| 2017/0169436 A1* | 6/2017 | Ur | G06Q 30/01 |
| 2019/0167831 A1* | 6/2019 | Chan | A61L 9/125 |
| 2019/0196576 A1* | 6/2019 | Saarinen | G06V 20/20 |
| 2021/0248664 A1* | 8/2021 | Maeda | G06Q 30/0282 |

FOREIGN PATENT DOCUMENTS

| | | |
|---|---|---|
| JP | 2006-280748 A | 10/2006 |
| JP | 2009-090159 A | 4/2009 |
| JP | 2011-215462 A | 10/2011 |
| JP | 2014-000183 A | 1/2014 |
| JP | 2014-219644 A | 11/2014 |

* cited by examiner

| User's state | Presented scent | Degree of acceptance |
|---|---|---|
| During meal | Citrus scent | × |
| | Herbal scent | △ |
| | Soap scent | × |
| | Sweet scent | × |
| At time of waking up | Citrus scent | ○ |
| | Herbal scent | △ |
| | Soap scent | × |
| | Sweet scent | × |
| During sleep | Citrus scent | × |
| | Herbal scent | ○ |
| | Soap scent | × |
| | Sweet scent | ○ |

INFORMATION PROCESSING APPARATUS AND INFORMATION PROCESSING METHOD

CROSS REFERENCE TO RELATED APPLICATIONS

This application is a U.S. National Phase of International Patent Application No. PCT/JP2019/035353 filed on Sep. 9, 2019, which claims priority benefit of Japanese Patent Application No. JP 2018-208706 filed in the Japan Patent Office on Nov. 6, 2018. Each of the above-referenced applications is hereby incorporated herein by reference in its entirety.

TECHNICAL FIELD

The present technology relates to an information processing apparatus, an information processing method, and a program that are capable of controlling the output of a scent.

BACKGROUND ART

Conventionally, an apparatus that diffuses a desired scent into a space to present a relaxation effect to a user, such as an aroma diffuser, or an apparatus that improves a sense of immersion by presenting a scent, such as a 4DX theater, exist as an apparatus using a scent (perfume volatilization apparatus).

Regarding the perfume volatilization apparatus, an apparatus that includes a plurality of scent sources to variously control an attached fan, to thereby vary the scent and improve the quality of the scent presentation as disclosed in Patent Literature 1 below, for example, has been proposed as an apparatus that changes the output of the perfume volatilization apparatus in accordance with an external environment.

Further, regarding an apparatus that emits a scent for the purpose of presenting a sense of immersion, a device that changes the output of the apparatus in accordance with an image or the like to be displayed as shown in Patent Literature 2 below has been proposed.

In addition, Patent Literature 3 below has disclosed a scent generating apparatus that judges a user state when a predetermined scent generation time such as a preset time or a timing at which a person is detected is reached, and learns the correspondence between the scent generation time and the user state, to thereby learn what kind of state the user tends to be at what time and generate an optimal scent on the basis of the learned tendency.

CITATION LIST

Patent Literature

Patent Literature 1: Japanese Patent Application Laid-open No. 2002-369872
Patent Literature 2: Japanese Patent Application Laid-open No. 2011-215462
Patent Literature 3: Japanese Patent Application Laid-open No. 2002-369872

DISCLOSURE OF INVENTION

Technical Problem

However, in the technologies described in Patent Literatures 1 to 3 above, in a case where a plurality of users exist in the same space, the optimal scent differs for each user, but such a difference is not considered.

In view of the above-mentioned circumstances, it is an object of the present technology to provide an information processing apparatus, an information processing method, and a program that are capable of controlling the output of a scent for each of a plurality of users existing in the same space.

Solution to Problem

In order to accomplish the above-mentioned object, an information processing apparatus according to an embodiment of the present technology includes an input unit and a control unit. Sensing information sensed in a predetermined space is input into the input unit. The control unit controls, in accordance with a result obtained by analyzing states or attributes of a plurality of users existing in the space on a basis of the sensing information, output of a scent from the scent output apparatus to each of the users for each user.

With this configuration, the information processing apparatus is capable of controlling the output of the scent for each of the plurality of users existing in the same space. Here, the state of the user includes, for example, a state of a smell surrounding the user's position, a behavior currently performed by the user, an active state (eating, sleeping, at time of waking up, at time of going to bed, or the like), and the like. Further, the attribute of the user includes, for example, gender, age, nationality, allergy information, a presence state in the room, and the like.

The control unit may change kind and intensity of the scent in accordance with the state or the attribute of the user.

With this configuration, the information processing apparatus is capable of outputting the scent of the kind and the intensity suitable to the user in accordance with the state or the attribute of the user.

The control unit may determine a degree of acceptance of each user for a plurality of different scents in accordance with the state or the attribute of each of the users and determine the kind or the intensity of the scent to be output to each of the users and whether to output to each user in accordance with the degree of acceptance.

With this configuration, the information processing apparatus determines the degree of acceptance of each user for the plurality of scents to be capable of controlling the output of the scent for each user more efficiently.

The scent output apparatus may include a plurality of scent output apparatuses arranged at different positions in the space, and the control unit may determine, on a basis of the sensing information, a scent output apparatus of the plurality of scent output apparatuses, which has a shortest arrival time of the scent at the user, as an apparatus for outputting the scent to each of the users.

With this configuration, the information processing apparatus is capable of outputting the scent in a shortest time to each of the users existing at different positions in the space.

In a case where a distance between at least two scent output apparatuses of the plurality of scent output apparatuses and one user of the plurality of users is equal or approximately equal, the control unit may determine, on a basis of face orientation information of the user obtained from the sensing information, a scent output apparatus of the two scent output apparatuses, which is closer in a face orientation of the user, as an apparatus for outputting the scent.

With this configuration, the information processing apparatus is capable of selecting a scent output apparatus of the plurality of scent output apparatuses, which is capable of most effectively providing the scent to the user.

The control unit may determine the arrival time on a basis of wind direction information between each of the users and each of the scent output apparatuses, the wind direction information being obtained from the sensing information.

With this configuration, in a case where some wind blows in the space, the information processing apparatus is capable of more effectively providing the user with the scent as compared to a case of selecting a scent output apparatus that exists at a position simply closer to the user.

The control unit may output a video or audio associated with the scent before or during output of the scent to each of the users.

With this configuration, the information processing apparatus is capable of causing the user to get the scent more efficiently by combining the scent with another modal of the video or audio.

The control unit may output notification information for notifying of a direction in which the scent is generated before or during output of the scent to each of the users.

With this configuration, the information processing apparatus is capable of causing the user to get the direction in which the scent is generated and to get the scent efficiently.

In a case where content associated with the scent is input by the input unit, the control unit may determine a user of the plurality of users, who is an output target of the scent, on a basis of information included in the content and control the output of the scent for each of a user who is the output target and a user who is not the output target.

With this configuration, the information processing apparatus is capable of performing different control in accordance with whether or not the user is the output target of the content including the scent.

The control unit may output information indicating presence of the scent together with the content on a basis of the state or the attribute of each user in a case where it is determined that output of the scent associated with the content is impossible.

With this configuration, the information processing apparatus is capable of preventing the user from feeling discomfort by notifying the user of at least the presence of the scent associated with the content even if it is determined that the scent associated with the content cannot be output.

The content may include first content associated with a first scent and second content associated with a second scent, which are consecutively reproducible. In this case, the control unit may control an output timing of the first scent such that the first scent arrives at each of the users at a time of reproduction start of the first content and control an output timing of the second scent and an output stop timing of the first scent such that the second scent arrives at each of the users at a time of reproduction start of the second content.

With this configuration, even if a plurality of types of content is reproduced together with the scent, the information processing apparatus is capable of causing the user to get the scent associated with each type of content at a timing when the scent is synchronized with the reproduction start of each type of content.

The control unit may compare a reproduction time of the first content or the second content with an arrival time at each of the users from output of the first scent or the second scent, and stop the output of the first scent or the second scent in a case where the reproduction time is shorter than the arrival time.

With this configuration, the information processing apparatus is capable of preventing a case where the user gets a scent not associated with the content and is confused due to a time-lag of the arrival time of the scent.

In a case where it is determined that there is a possibility that a plurality of scents to be output to the respective users is mixed on a basis of the sensing information, the control unit may output the plurality of scents at predetermined time intervals or output another one of the scents at a timing when it is determined that intensity of output one of the scents becomes equal to or lower than a threshold on a basis of the sensing information.

With this configuration, the information processing apparatus is capable of preventing the different scents for the plurality of users from being mixed, which would make the user uncomfortable.

An information processing method according to another embodiment of the present technology includes:

receiving input of sensing information sensed in a predetermined space; and controls, in accordance with a result obtained by analyzing states or attributes of a plurality of users existing in the space on a basis of the sensing information, output of a scent from a scent output apparatus to each of the users for each user.

A program according to still another embodiment of the present technology causes the information processing apparatus to execute:

a step of receiving input of sensing information sensed in a predetermined space; and a step of controlling, in accordance with a result obtained by analyzing states or attributes of a plurality of users existing in the space on a basis of the sensing information, output of a scent from a scent output apparatus to each of the users for each user.

Advantageous Effects of Invention

As described above, in accordance with the present technology, it is possible to control the output of a scent for each of a plurality of users existing in the same space. However, the above-mentioned effects should not be construed to limit the present technology.

MODE(S) FOR CARRYING OUT THE INVENTION

Hereinafter, embodiments according to the present technology will be described with reference to the drawings.

First Embodiment

First, a first embodiment of the present technology will be described.

[Overview of System]

Figure 1:
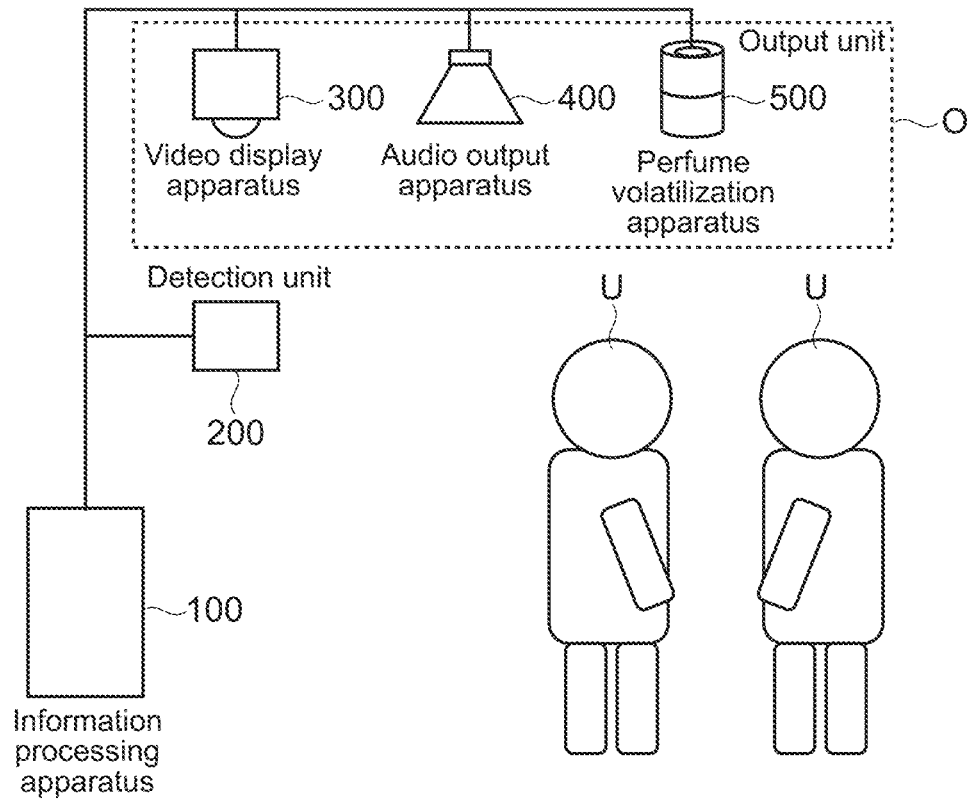
FIG. 1 A diagram showing a configuration of a perfume volatilization system according to a first embodiment of the present technology.

FIG. 1 is a diagram showing a configuration of a perfume volatilization system according to an embodiment of the present technology.

As shown in the figure, the perfume volatilization system according to this embodiment includes an information processing apparatus 100, a detection unit 200 as an input unit of information, a video display apparatus 300 as an output unit O that presents information to users U, an audio output apparatus 400, and a perfume volatilization apparatus 500.

Alternatively, in addition to the above, an apparatus that presents a tactile sense or the like may be included as the output unit.

The information processing apparatus 100 is, for example, a computer such as a personal computer or a smartphone.

The detection unit 200 includes a group of sensors that detect a user and an environmental state of a space in which the user exists.

The detection unit 200 is constituted by, for example, a sensor that acquires image and depth information of a space in which the information processing apparatus 100 is installed, such as a depth camera and an electronic camera, and a sensor that acquires invisible information such as a smell sensor and a anemometer.

The detection unit 200 and the output unit O are connected to the information processing apparatus 100. The connection method may be wireless or wired, and does not necessarily have to be in the same space as the information processing apparatus 100.

The detection unit 200 (respective sensors constituting the detection unit 200) is installed in a position capable of detecting the user and the environmental state to be detected.

The video display apparatus 300 receives a display image from the information processing apparatus 100, and performs video display on an area to be displayed. The video display apparatus 300 may be a projector, a head-up display, a retinal projection display, or the like, or may be a fixed monitor such as a liquid-crystal display (LCD) or an organic electro-luminescence (EL) display.

Further, the video display apparatus 300 may have a function such as a zoom mechanism, an auto focus function, and a display area changing function. Further, a single video display apparatus 300 may be provided or a plurality of video display apparatuses 300 may be provided and the video display apparatus(es) 300 may be fixed or may be movable. Further, the video display apparatus 300 may be a user-wearable device such as a head-mounted display.

The sound output apparatus 400 is mainly a speaker, and receives input sound from the information processing apparatus 100 and outputs the input sound to generate a sound image. As the speaker, a paper cone type, a piezoelectric type, an ultrasonic type, or the like can be used. Further, the audio output apparatus 400 may be a plurality of sound output apparatuses or may be a user-wearable device such as headphones or the like.

The perfume volatilization apparatus 500 is an apparatus that outputs a specific scent by diffusing the built-in perfume into the space. The perfume volatilization apparatus 500 receives input data (selection and output intensity of perfume) from the information processing apparatus 100 and outputs the corresponding scent.

The perfume volatilization apparatus 500 is a stationary (table top type) apparatus having a shape like a smart speaker, for example, but may be a wearable device.

The perfume volatilization apparatus 500 has, as its internal configuration, a perfume as a source of a scent and a volatilization apparatus that volatilizes the perfume. There may be a plurality of perfumes, and when a scent is generated, one of the perfumes may be used or the plurality of perfumes may be used in a composite manner. Further, a plurality of volatilization ports may be provided corresponding to different perfumes or a configuration in which the output directions of the plurality of volatilization ports may be movable in accordance with the position of the user, for example, may be employed.

The volatilization apparatus volatilizes a scent from a perfume by a method such as a heating method and an ultrasonic method. The volatilization apparatus may be accompanied by an apparatus that controls the diffusion direction of the scent, such as a separate blower. The scent may be presented to a specific place in a living space by using such a control apparatus or the effect of the scent may be weakened by only blowing the air. Further, the volatilization apparatus may also be a user-wearable device, for example, configured as a part of a head-mounted display or smart glass.

The blower may be an electric fan, a ventilation fan, or the like in the living space. Further, if there are mechanisms to open windows automatically, they may be utilized as blowers.

The detection unit 200 is mainly constituted by a group of sensors such as an electronic camera. The group of sensors includes the following ones.

Those that acquire images and information similar to images such as an electronic camera, a depth sensor, and a thermal camera Those that acquire invisible information (environmental evaluation sensors) such as a microphone, a smell sensor, and an anemometer Using the sensing data of these groups of sensors, the information processing apparatus 100 gets, for example, the number of users, position(s), face (nose) orientation, personal recognition, behavior state estimation, a wind direction of the environment, and the like. Alternatively, the information processing apparatus 100 may also get the position of the group of apparatuses constituting the above-mentioned output unit through the group of sensors and may read and store coordinate data of the group of sensors in advance in a case where the group of apparatuses is fixed in advance.

An example of each sensor is shown below.

The electronic camera captures an image of an environment in which information is presented, and acquires image information. There may be a single or a plurality of electronic cameras. Further, the imaging wavelength is not limited to the visible light range, may include ultraviolet and infrared light ranges, may be limited to a specific wavelength region, or it may be used as a sensor that measures only illuminance.

The depth sensor acquires a distance between the center and an object. The acquisition method therefor may be a time of flight (ToF) method, an ultrasonic method, or the like. The data to be acquired may be in a two-dimensional data format or in a time-series data format at the same point.

The thermal camera acquires a heat generation state of the environment. In addition to or instead of the thermal camera, a microphone or the like may acquire data related to a sound of the environment.

The environmental evaluation sensor measures a smell level through the smell sensor or the like and measures air volume through the anemometer or the like.

The smell sensor utilizes a semiconductor system, a crystal resonator system, a surface stress system, or the like, and a plurality of sensors may be combined in a case where the types of gas that the smell sensor can react are limited. Further, in a case where the occurrence of a smell is predicted by behavior estimation of the user U or the like, the smell may be estimated on the basis of the estimated behavior. For example, it can be estimated that a smell is generated during a meal.

The air volume is measured by an anemometer of an ultrasonic type, a hot wire type, or the like. Further, local air volume may be estimated by another group of sensors. For example, in a case where the user U uses a dryer, it is conceivable that turbulence is generated in the periphery thereof. Further, in a case where the ventilation fan is driven, it can be estimated that turbulence is generated in the periphery thereof.

Alternatively, the detection unit 200 may be a wearable device worn by the user. More specifically, the detection unit 200 may be a pulse sensor that measures the pulse rate, a sweat sensor that detects the sweating amount, a body thermometer, or the like.

[Hardware Configuration of Information Processing Apparatus]

Figure 3:
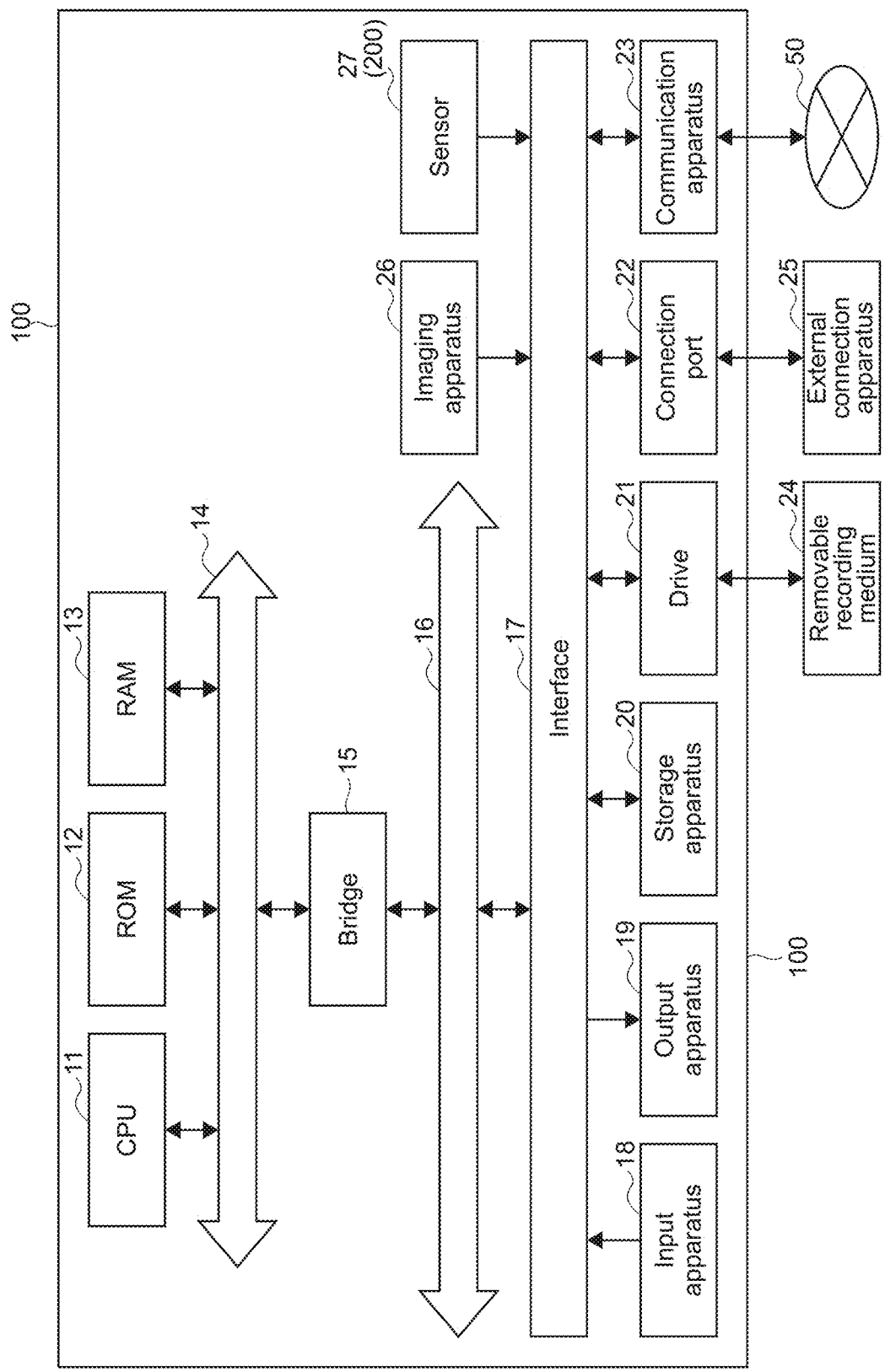
FIG. 3 A diagram showing a hardware configuration of an information processing apparatus of the perfume volatilization system according to the first embodiment.

FIG. 3 is a diagram showing a hardware configuration of the information processing apparatus 100.

As shown in the figure, the information processing apparatus 100 includes a central processing unit (CPU) 11, a read only memory (ROM) 12, and a random access memory (RAM) 13. Further, the information processing apparatus 100 may include a host bus 14, a bridge 15, an external bus 16, an interface 17, an input apparatus 18, an output apparatus 19, a storage apparatus 20, a drive 21, a connection port 22, and a communication apparatus 23. Further, the information processing apparatus 100 may include an imaging apparatus 26 and a sensor 27 as necessary. The information processing apparatus 100 may include processing circuits such as a digital signal processor (DSP), an application specific integrated circuit (ASIC), and a field-programmable gate array (FPGA) instead of or together with the CPU 11.

The CPU 11 functions as an arithmetic processing unit and a control unit and controls the overall operation of the information processing apparatus 100 or a part thereof in accordance with various programs recorded on the ROM 12, the RAM 13, the storage apparatus 20, or a removable recording medium 24. The ROM 12 stores programs and arithmetic parameters used by the CPU 11. The RAM 13 primarily stores a program used in running of the CPU 11, parameters that change accordingly in running thereof, and the like. The CPU 11, the ROM 12, and the RAM 13 are connected to one another through the host bus 14 including an internal bus such as a CPU bus. In addition, the host bus 14 is connected via the bridge 15 to the external bus 16 such as a peripheral component interconnect/interface (PCI) bus.

The input apparatus 18 is an apparatus operated by the user, such as a touch panel, a physical button, a switch, and a lever, for example. The input apparatus 18 may be, for example, a remote control apparatus using infrared rays or other radio waves or may be an external connection apparatus 25 such as a smartphone and a smartwatch compatible with the operation of the information processing apparatus 100. The input apparatus 18 includes an input control circuit that generates an input signal on the basis of information input by the user and outputs the generated input signal to the CPU 11. By operating the input apparatus 18, the user inputs various types of data to the information processing apparatus 100 or instructs a processing operation.

The output apparatus 19 is configured as an apparatus capable of notifying the user of obtained information by using a sense such as a sense of sight, a sense of hearing, and a sense of touch. The output apparatus 19 can be, for example, a display apparatus such as an LCD and an organic EL display, an audio output apparatus such as a speaker, or the like. The output apparatus 19 outputs the result acquired by the processing of the information processing apparatus 100 as a video such as a text and an image, audio such as a voice and a sound, a vibration, or the like.

The output apparatus 19 may be replaced by the video display apparatus 300 and the audio output apparatus 400, or may be provided separately therefrom.

The storage apparatus 20 is a data storage apparatus configured as an example of a storage unit of the information processing apparatus 100. The storage apparatus 20 includes, for example, a magnetic storage device such as a hard disk drive (HDD), a semiconductor storage device, an optical storage device, a magneto-optical storage device, and the like. The storage apparatus 20 stores, for example, programs and various types of data executed by the CPU 11, various types of data acquired from the outside, and preset information of the above-mentioned projection area A.

The drive 21 is a reader/writer for the removable recording medium 24 such as a magnetic disk, an optical disc, a magneto-optical disc, and a semiconductor memory, and is built in or externally attached to the information processing apparatus 100. The drive 21 reads information recorded on the mounted removable recording medium 24 and outputs the read information to the RAM 13. Further, the drive 21 writes a record in the mounted removable recording medium 24.

The connection port 22 is a port for connecting the apparatus to the information processing apparatus 100. The connection port 22 can be, for example, a universal serial bus (USB) port, an IEEE1394 port, a small computer system interface (SCSI) port, or the like. Alternatively, the connection port 22 may be an RS-232C port, an optical audio terminal, a high-definition multimedia interface (HDMI) (registered trademark) port, or the like. By connecting the external connection apparatus 25 to the connection port 22, various types of data can be exchanged between the information processing apparatus 100 and the external connection apparatus 25.

The communication apparatus 23 is, for example, a communication interface constituted by a communication device or the like for connecting the output unit, the detection unit 200, and the like via a network. The communication apparatus 23 may be, for example, a communication card or the like for a local area network (LAN), Bluetooth (registered trademark), Wi-Fi, or a wireless USB (WUSB). Alternatively, the communication apparatus 23 may be a router for optical communication, a router for an asymmetric digital subscriber line (ADSL), a modem for various types of communication, or the like. The communication apparatus 23 sends and receives a signal and the like to and from the Internet or other communication apparatuses, for example, by using a predetermined protocol such as TCP/IP. Further, a communication network 50 connected to the communication apparatus 23 is a wired or wireless network, and can include, for example, the Internet, a home LAN, infrared communication, radio wave communication, satellite communication, and the like.

The imaging apparatus 26 is, for example, a camera that images a real space and generates a captured image by using various members such as an image pickup device such as a complementary metal oxide semiconductor (CMOS) and a charge coupled device (CCD) and a lens for controlling forming of an object image in the image pickup device. The imaging apparatus 26 may take a still image or may take a moving image.

The sensor 27 is configured as a part of the detection unit 200, and is various sensors such as an acceleration sensor, an angular velocity sensor, a geomagnetic sensor, an illuminance sensor, a temperature sensor, an atmospheric pressure sensor, a depth sensor, and a sound sensor (microphone), for example. The sensor 27 acquires, for example, information regarding a state of the information processing apparatus 100 itself such as an attitude of a casing of the information processing apparatus 100 and information regarding a peripheral environment of the information processing apparatus 100 such as brightness and noise around the information processing apparatus 100. Alternatively, the sensor 27 may also include a GPS receiver that receives a global positioning system (GPS) signal to measure latitude, longitude, and altitude of the apparatus.

Each of the above-mentioned components may be configured with a general-purpose member or may be configured as hardware specialized in the function of each component. Such a configuration may be changed as appropriate in a manner that depends on the technical level at the time of implementation.

[Functional Block Configuration of Information Processing Apparatus]

Figure 2:
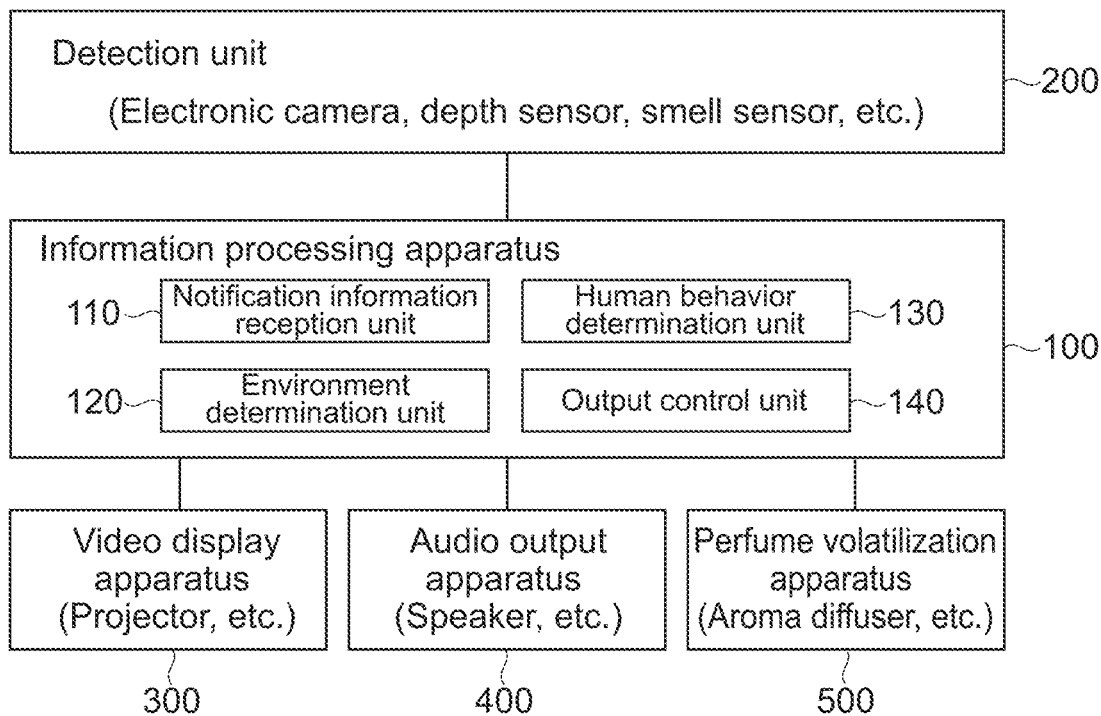
FIG. 2 A diagram showing a hardware configuration, a functional block configuration, and a functional block configuration of the perfume volatilization system according to the first embodiment.

Next, functional blocks of the information processing apparatus 100 will be described. As shown in FIG. 2, the information processing apparatus 100 includes a notification information reception unit 110, an environment determination unit 120, a human behavior determination unit 130, and an output control unit 140 as the functional blocks.

The notification information reception unit 110 receives information that the information processing apparatus 100 should notify of a user of the plurality of users U, who is a notification target. The information may be read from a service on the Internet, another external apparatus, or a database or may be generated in the information processing apparatus 100.

The information received by the notification information reception unit 110 includes contents to be output to each output apparatus of the output unit O and is specifically video data, audio data, and scent generation data (selection of a perfume, intensity and duration time of a scent, and the like).

Alternatively, in a case where the information processing apparatus 100 controls a group of devices installed in the environment, the notification information reception unit 110 may receive control information therefor. For example, in a case where there is a blower installed separately from the perfume volatilization apparatus 500 and a scent generated from the perfume volatilization apparatus 500 is presented in a specific direction, the notification information reception unit 110 may receive control information and the information processing apparatus 100 may control the blowing direction and intensity of the blower for realizing the control operation. Alternatively, in a case where a room has to be ventilated, the notification information reception unit 110 may receive control information for controlling a ventilator installed in the room.

The environment determination unit 120 gets an environment state of a target user to which information is to be presented and other users on the basis of inputs from the various groups of sensors.

The human behavior determination unit 130 gets behavior states and attributes of the target user to which information is to be presented and the other users on the basis of inputs from the various groups of sensors.

The output control unit 140 selects the output apparatus of the output unit O associated with the information processing apparatus 100 and outputs the information on the basis of the information from the environment determination unit 120 and the human behavior determination unit 130 described above.

In a case where there are a plurality of output destinations of video and audio, the output control unit 140 may select an optimal place on the basis of the position of the user U or the like.

Although the positions of all the output apparatuses may be spatially coincident with each other, the information presentation to the sense of smell using a scent has less directivity as compared to the sense of vision and the sense of hearing. Therefore, for example, even if the position of the output video and the position of the selected perfume volatilization apparatus 500 are deviated from each other, it gives less discomfort. However, since the speed of information transmission is slower than that of video and audio, control different from that of video and audio is necessary for output control on the scent. Further, it is conceivable that information presentation to the sense of smell causes discomfort or the like in a case of presenting a scent not matching the state of the target user in addition to the sense of vision and the sense of hearing. Therefore, in information presentation using a scent, it is important to present an appropriate scent and an appropriate intensity at an appropriate timing in accordance with the state of the target user.

[Operation of Perfume Volatilization System]

Next, an operation of perfume volatilization system configured as described above will be described. The operation is performed by cooperation of hardware of the CPU 11, the communication unit, or the like of the information processing apparatus 100 and software stored in the ROM 12, the RAM 13, the storage apparatus 20, or the removable recording medium 24. Hereinafter, the description will be given assuming that the CPU 11 primarily performs the operation for the sake of convenience.

In order to describe a specific example of this embodiment, a basic operation as its premise will be described.

(Method of Determining Perfume Volatilization Apparatus)

First, a method of determining a perfume volatilization apparatus 500 that presents a scent to a target user in a case where a plurality of perfume volatilization apparatuses 500 exists in a space will be described.

In order to efficiently present the scent to the target user at an appropriate timing, it is basically desirable that the distance between the target user and the perfume volatilization apparatus 500 be shorter.

Figure 4A:
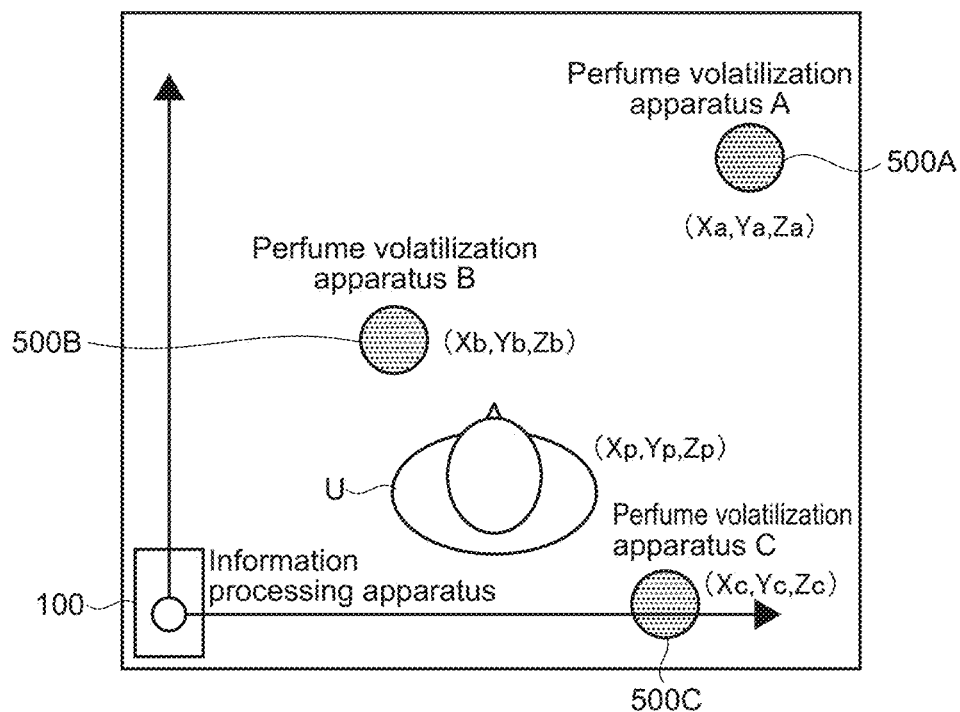
FIGS. 4A and 4B Diagrams describing a method of determining a perfume volatilization apparatus in the perfume volatilization system according to the first embodiment.
Figure 4B:
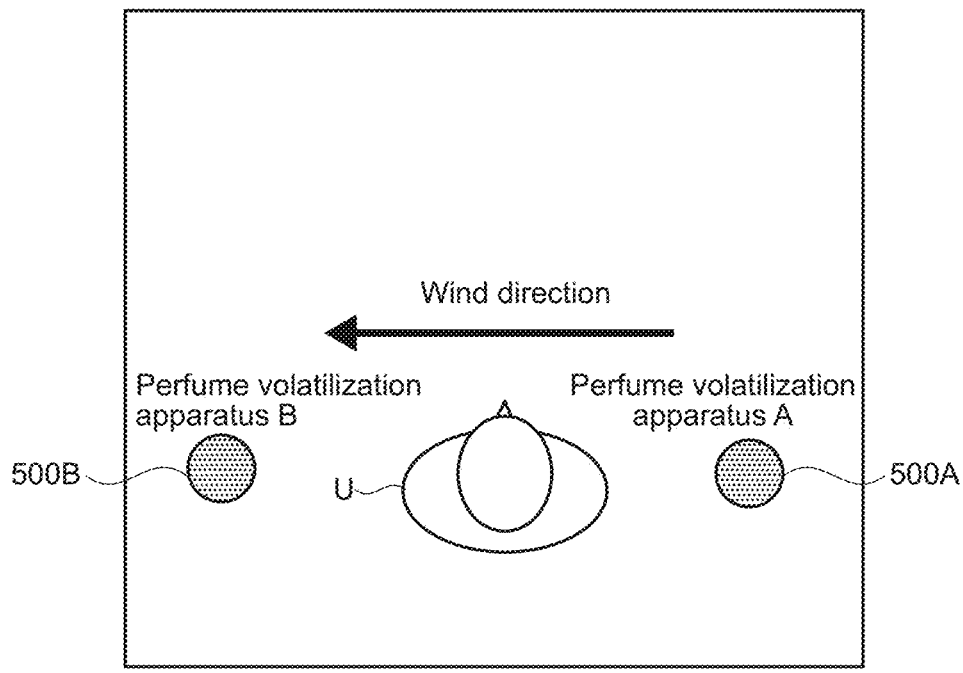
Figure 5:
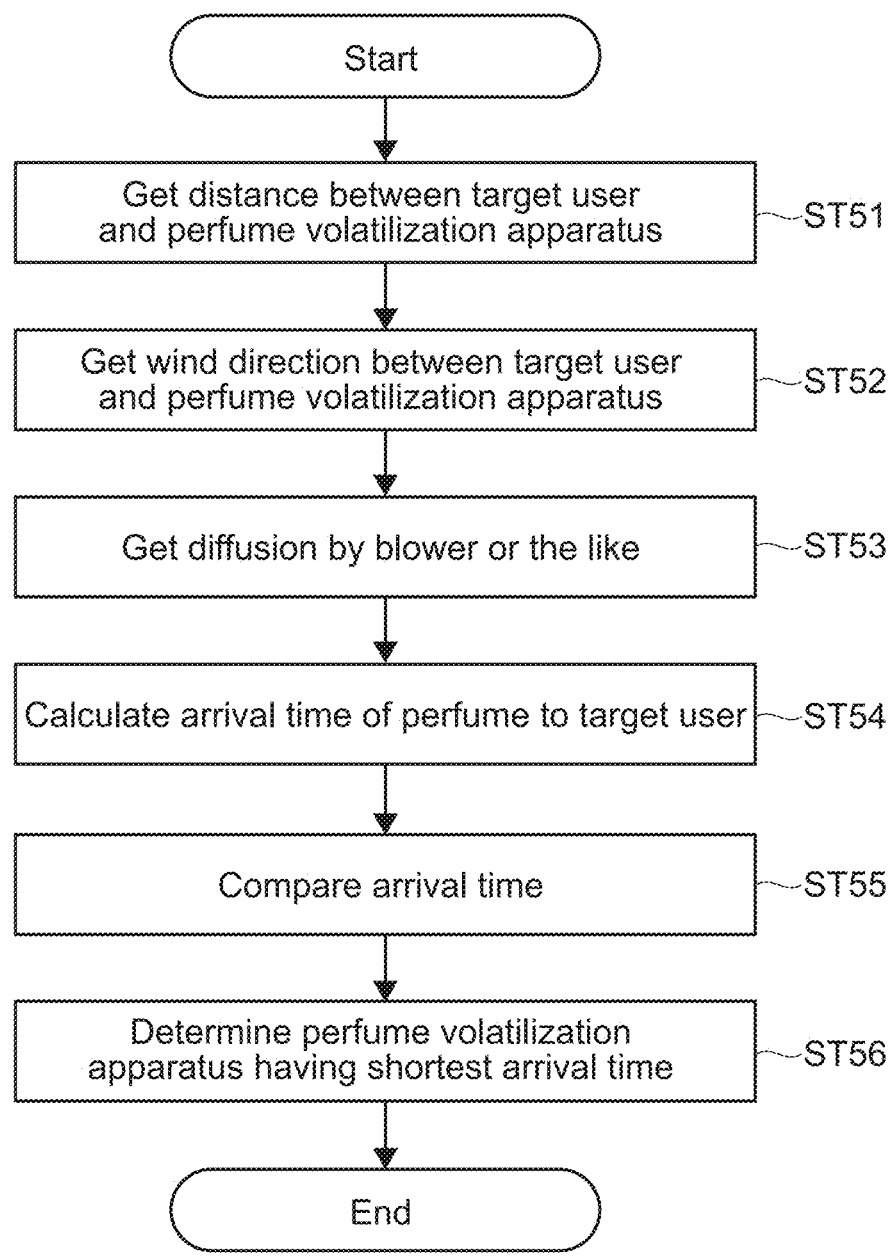
FIG. 5 A flowchart showing a flow of determination processing of the perfume volatilization apparatus in the perfume volatilization system according to the first embodiment.

FIGS. 4A and 4B are diagrams for describing the method of determining the perfume volatilization apparatus 500 and FIG. 5 is a flowchart showing a flow of determination processing of the perfume volatilization apparatus 500.

As shown in the FIG. 4A, it is assumed that the plurality of perfume volatilization apparatuses 500 exists in a certain space.

First, the CPU 11 of the information processing apparatus 100 gets the distances between the target user and the perfume volatilization apparatus 500 (Step 51).

A method of calculating the distance will be described below. In a case where XYZ space coordinates are determined using the position of the information processing apparatus 100 as the origin, a position (Xp, Yp, Zp) of the face of the target user U called from the detection unit 200 and the position of each of the perfume volatilization apparatuses A, B, and C (Xa, Ya, Za) in FIG. 4A are determined.

In this case, on the basis of the position of the target user U and the positions of the plurality of perfume volatilization apparatuses A to C, the CPU 11 calculates a distance between both. This is performed by the equation for calculating the distance between two points in the space.

As a result, it is found that the perfume volatilization apparatuses B and C are close to the target user U. It is assumed that the perfume volatilization apparatuses B and C are at the same distance from the user U. One closer to the person's nose is more perceptible because of the nature of the scent. Therefore, on the basis of the face orientation acquired from the detection unit 200, the CPU 11 selects the perfume volatilization apparatus B closer in the face orientation of the user U as an output target. The above is the basic method of selecting the apparatus.

Alternatively, in a case where the volatilization direction of the perfume has anisotropy, for example, in a case where the perfume volatilization apparatus 500 has a blower or in a case where a wind blows in the room, the CPU 11 may consider its anisotropy (Step 52).

For example, it is assumed that the wind in the space is flowing as shown in FIG. 4B. Further, it is assumed that the plurality of perfume volatilization apparatuses A and B is arranged on the left and right sides of the target user U in the room. The CPU 11 gets information regarding a wind flow from the sensing data of an air flow meter in the room through the environment determination unit 120. In this case, it is efficient and desirable to select the perfume volatilization apparatus A present in the wind. Therefore, in this instance, the CPU 11 sets the perfume volatilization apparatus A as the output apparatus in a case of presenting the scent. Thus, in a case of considering parameters such as winds that affect the arrival time of the perfume, the CPU 11 determines the perfume volatilization apparatus 500 on the basis of the arrival time of the perfume to the target user U, not the distance.

More specifically, as shown in FIG. 5, the CPU 11 gets the diffusion of the perfume by the blower or the like (Step 53) in addition to the wind direction (Step 52) and calculates the arrival time of the perfume to the target user U for each perfume volatilization apparatus 500 (Step 54).

Then, the CPU 11 compares the arrival times of the plurality of perfume volatilization apparatuses 500 (Step 55) and determines the perfume volatilization apparatus 500 having the shortest arrival time as an apparatus for outputting the perfume to the target user U (Step 56).

(Method of Controlling Output Intensity)

Next, a method of controlling the output intensity of the perfume will be described.

In a case where information is presented using a scent, it is necessary to output the scent having intensity that exceeds that of the scent of the surrounding environment. It is because in a case where the smell level of the environment is high, there is a possibility that the output of the scent to be presented may be insufficient and sufficient presentation may not be possible.

However, it is not always necessary to increase the intensity, and conversely, in a case where the smell level is low, the output may be too strong and it may reduce the user's comfort.

Therefore, the CPU 11 must perform the output control according to the environment. For example, in a case where a smell sensor is installed in the space, the CPU 11 refers to the intensity and controls the output. Alternatively, since the perception of a scent varies from person to person, the CPU 11 may adjust the strength on the basis of the gotten user attributes and environmental information. For example, in a case where a strong scent is preferable on the basis of a country or region attribute, the CPU 11 may consider such an attribute.

Further, a behavior state of the target user U is one of items that should be considered in the output control of the scent. For example, in a case where the target user U is about to enter sleep, it is undesirable to present a scent that promotes wakefulness. Further, in a case where the target user is eating, it is inappropriate to use a strong scent.

Thus, it is important to perform the output control according to the state of the target user U in the information presentation using a scent.

EXAMPLES

In view of the above, specific examples of this system will be described below.

Figures 6, 7:
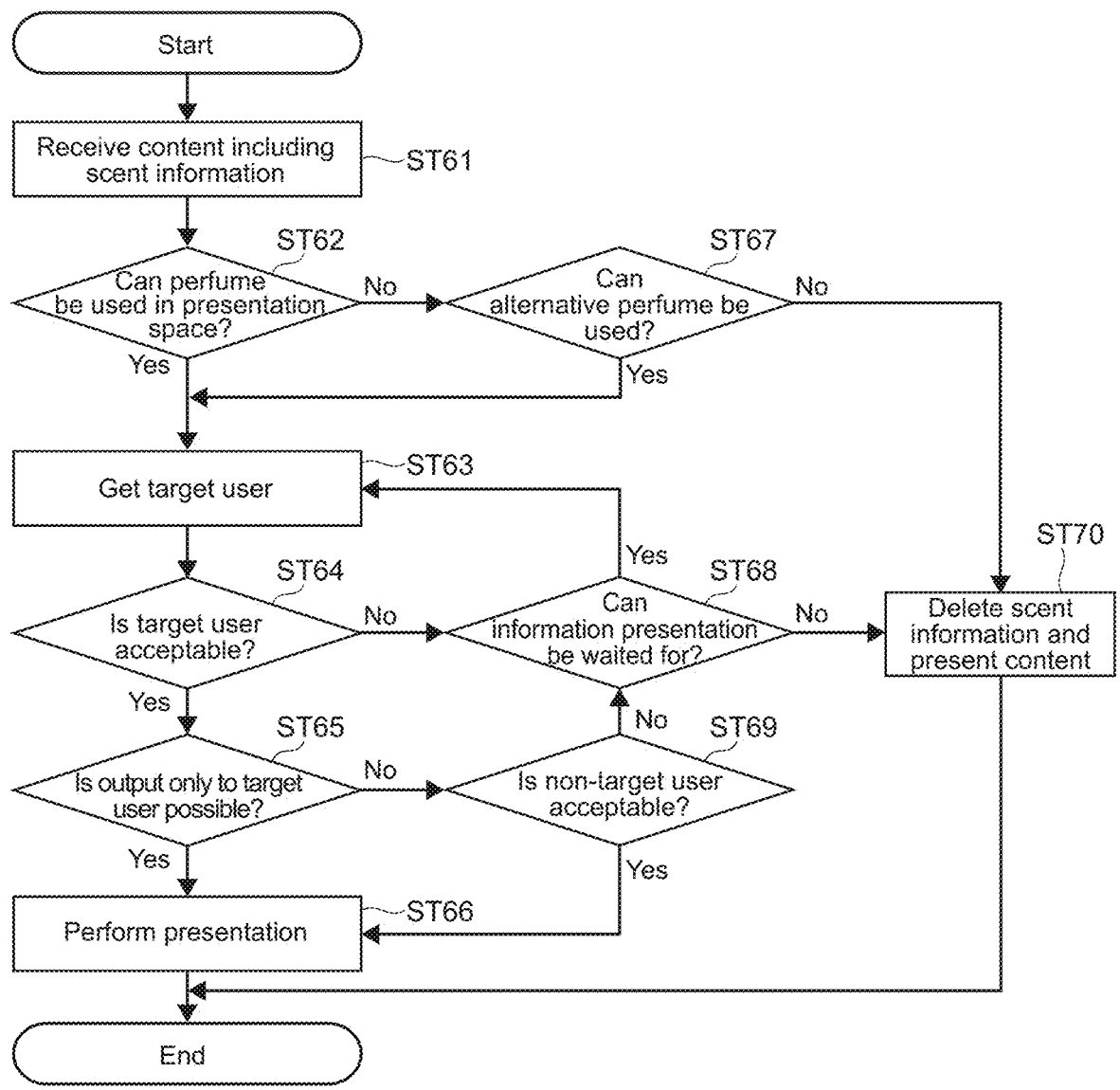
FIG. 6 A flowchart showing a general flow of perfume volatilization processing in the perfume volatilization system according to the first embodiment.
FIG. 7 A table showing an example of user attribute information to which the information processing apparatus refers in the perfume volatilization system according to the first embodiment.

FIG. 6 is a flowchart showing a flow of perfume volatilization processing according to this embodiment.

As shown in the figure, the CPU 11 first receives content including scent information (associated with scent information) (Step 61). As described above, the information includes video, audio, and scent information. Alternatively, the information may also include other information regarding a sense of touch or the like. It is assumed that the content does not need to include all of these pieces of information, but includes at least the scent information.

Here, it is assumed that a video message advertisement including the scent information is provided as the content, but other content such as a personal video message other than the advertisement may be provided. Further, it is conceivable that the content includes video, audio, and scent information.

The CPU 11 first determines whether or not the perfume indicated by the information can be used in a space in which it is to be presented (Step 62). The determination is performed by performing comparison with attribute information to be described later.

In a case where it is determined that the perfume cannot be used (No), the CPU 11 determines whether or not an alternative perfume can be used (Step 67). In a case where it is determined that the alternative perfume does not exist (No), the scent information is deleted and the content is output (Step 70).

In a case where it is determined that the perfume can be used in the space in which it is to be presented (Yes in Step 62), the CPU 11 gets a target user to which the content is to be presented (Step 63). It is for performing control both for efficiently presenting the scent to the target user and avoiding presentation of the scent to users other than the target user.

Specifically, in a case of a video message as in this example, the CPU 11 may determine the target user on the basis of a destination or receiver's address of the message. Further, in a case where the content to be notified has been generated using a user's explicit instruction as a trigger, the target is the user who has made the instruction.

Further, the CPU 11 calls identifiers and attributes of users in the same space for getting the target user. For example, in a case where a target user or a non-target user has a matter of restricting the use of the perfume associated with the content, such as an allergy, the CPU 11 needs to present the content by changing the kind of scent or deleting the scent, and should consider a preference derived from the attributes if any.

The attribute information of the user includes gender, age, nationality, allergy information, and the like, and is, for example, information as shown in FIG. 7. The information processing apparatus 100 stores such information as a database in the storage apparatus 20 or an external storage in advance, and the CPU 11 monitors a presence state of each user in the room, which is included in the database in real time, to thereby operate it.

In a case where target users are determined, the CPU 11 detects the positions of those users. The positions are gotten from group of sensors installed in the environment. At this time, the CPU 11 detects not only the positions but also the face orientations.

Figures 8, 9:
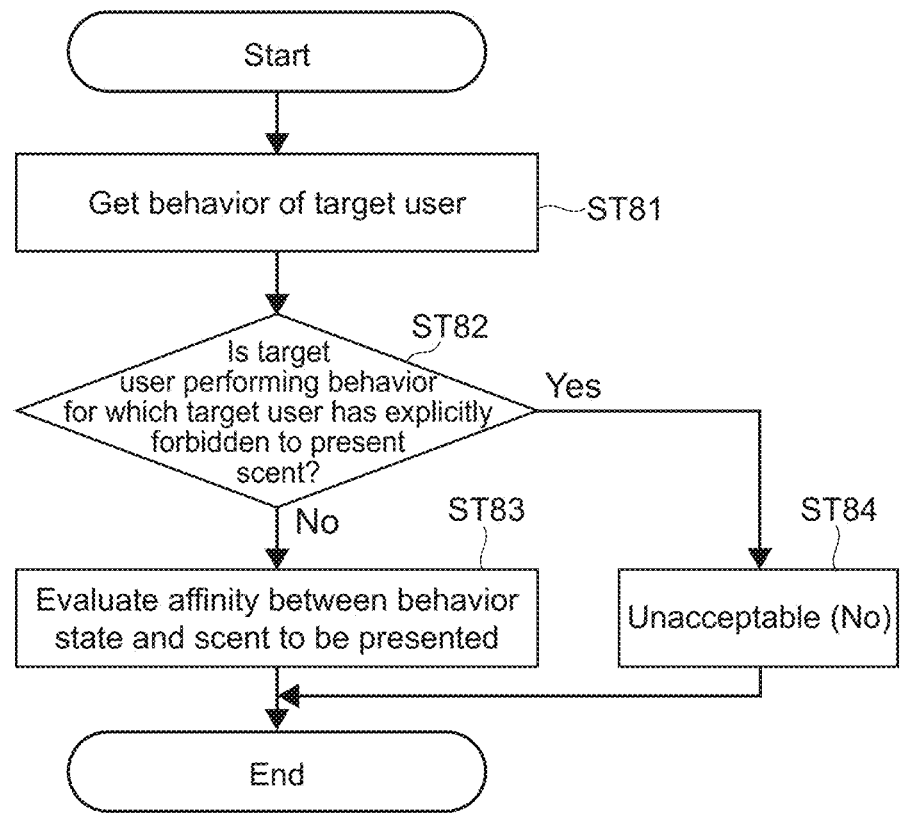
FIG. 8 A flowchart showing a flow of determination processing as to whether or not a target user can accept a scent in the perfume volatilization system according to the first embodiment.
FIG. 9 A table showing the correspondence between the user's state and the acceptance/unacceptance of each scent in the perfume volatilization system according to the first embodiment.

The CPU 11 then determines for the target users whether or not the content presentation including the scent is acceptable (Step 64). FIG. 8 is a flowchart showing determination processing as to the acceptance/unacceptance.

As shown in the figure, the CPU 11 first gets a behavior state of the target user on the basis of sensing information from the detection unit 200 (Step 81). The behavior state is a behavior performed by the target or an active state. For example, the behavior state is "during sleep", "during a meal", "during nap", or the like.

Subsequently, the CPU 11 determines whether or not the gotten behavior is a behavior for which the target user has forbidden to present the scent in advance (Step 82). For this determination, the attribute information of the user includes information regarding the behavior for which the user has forbidden to present the scent (for example, forbidding to present the scent during a meal and the like).

In a case where it is determined that the gotten behavior is a behavior for which the presentation of the scent is forbidden (Yes), the CPU 11 determines that the target user is unacceptable (No) in Step 64 of FIG. 6 (Step 84).

On the other hand, in a case where it is determined that the gotten behavior is a behavior for which the presentation of the scent is not forbidden (No), the CPU 11 evaluates the affinity between the scent to be presented and the state of the target user by referring to a table in which the affinity between the scent and the active state is evaluated as shown in FIG. 9, and calculates a degree of acceptance of the target user (Step 83).

For example, during a meal, a soap or sweet scent is unacceptable while a mild scent such as a herbal scent is acceptable, though the degree of acceptance is low because of the characteristics of "during a meal". On the other hand, it is assumed that the affinity with a citrus scent is high at the time of waking up. In this manner, the CPU 11 evaluates the degree of acceptance of the target user on the basis of the affinity between the state of the target user and the scent to be presented. The state in which the degree of acceptance is "x" in the table corresponds to a case where it is determined in Step 64 that the target user is unacceptable (No).

Since such evaluation affects the attributes of individuals, the CPU 11 may change the evaluation method in view of the attributes of the target users. For example, in the case of a target user who likes sweet scents at the time of waking up, the CPU 11 may reflect them as an evaluation item in advance. Also, spice scents are likely to be acceptable even during a meal in a case where the target user are eating Indian food, for example. Thus, the CPU 11 may evaluate the affinity between the scent and the state of the user in accordance with the more specific state of the user.

In a case where it is determined that the scent is unacceptable to the target user (No in Step 64), the CPU 11 determines whether or not the target user can wait for the content to be presented (Step 68). For example, in a case where the target user has forbidden to present scents during a meal, the CPU 11 waits until the meal is finished, and in a case where the content is content having real-time or urgent characteristics, it is determined that the standby is not possible.

In a case where it is determined that the target user can wait for the content to be presented (Yes), the CPU 11 returns to Step 63 and repeats the subsequent processing. On the other hand, in a case where it is determined that the target user cannot wait for the content to be presented (No), the scent information is deleted and the content is output (Step 70). Alternatively, the CPU 11 may limit the output strength of the scent to a minimum value instead of deleting the scent information.

In a case where it is determined that the target user is acceptable for the scent (Yes in Step 64), the CPU 11 determines whether or not the perfume volatilization apparatus 500 capable of outputting the scent only to the target user exists (Step 65).

Figure 10A:
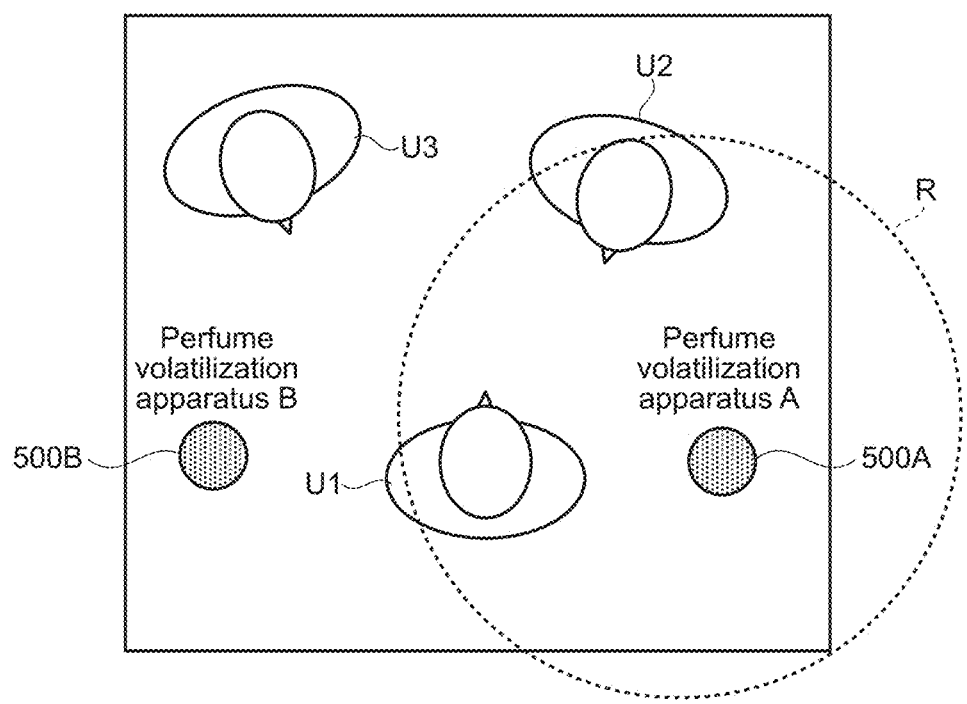
FIGS. 10A and 10B Diagrams for describing determination processing as to whether or not presentation of a scent to a plurality of users is possible in the perfume volatilization system according to the first embodiment.

For example, a state as shown in FIG. 10A is assumed. In this figure, a user U1 and a user U2 are the target users, and a user U3 is the non-target user. In a case where the perfume is concentrically volatilized from the perfume volatilization apparatus A in the figure, only the target users U1 and U2 can be notified of the scent.

Figure 10B:
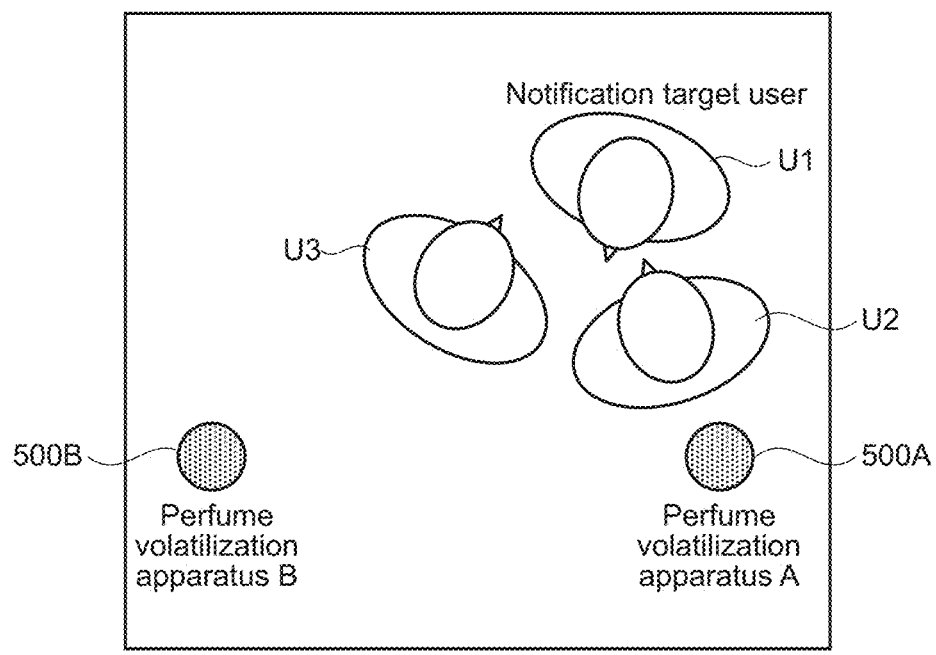

On the other hand, in a case where the non-target users U2 and U3 exist in the vicinity of the target user U1 as shown in FIG. 10B, it is difficult to present the scent only to the target user U1.

Therefore, in the state of FIG. 10A, since it can be determined that the scent can be presented only to the target user (Yes in Step 65), the CPU 11 causes the perfume volatilization apparatus 500 to output the content including the scent to the target user (Step 66).

When presenting the content, the CPU 11 may change the intensity of the scent in accordance with the degree of acceptance described above. For example, the CPU 11 may reduce the intensity of the scent to 50% of the prescribed value in a case where the degree of acceptance of the target user for the scent to be presented is Δ. Such control of the output value is carried out by using the concentration of the perfume, the volatilization time, or the like.

In the example of FIG. 10A, the perfume volatilization apparatus A presents the scent to the two target users U1 and U2. At this time, in a case where the degree of acceptance of one of the target users U1 and U2 for the scent to be presented is Δ and the degree of acceptance of the other is o, the CPU 11 prefers Δ, and outputs the scent having the intensity reduced, for example.

Figure 11:
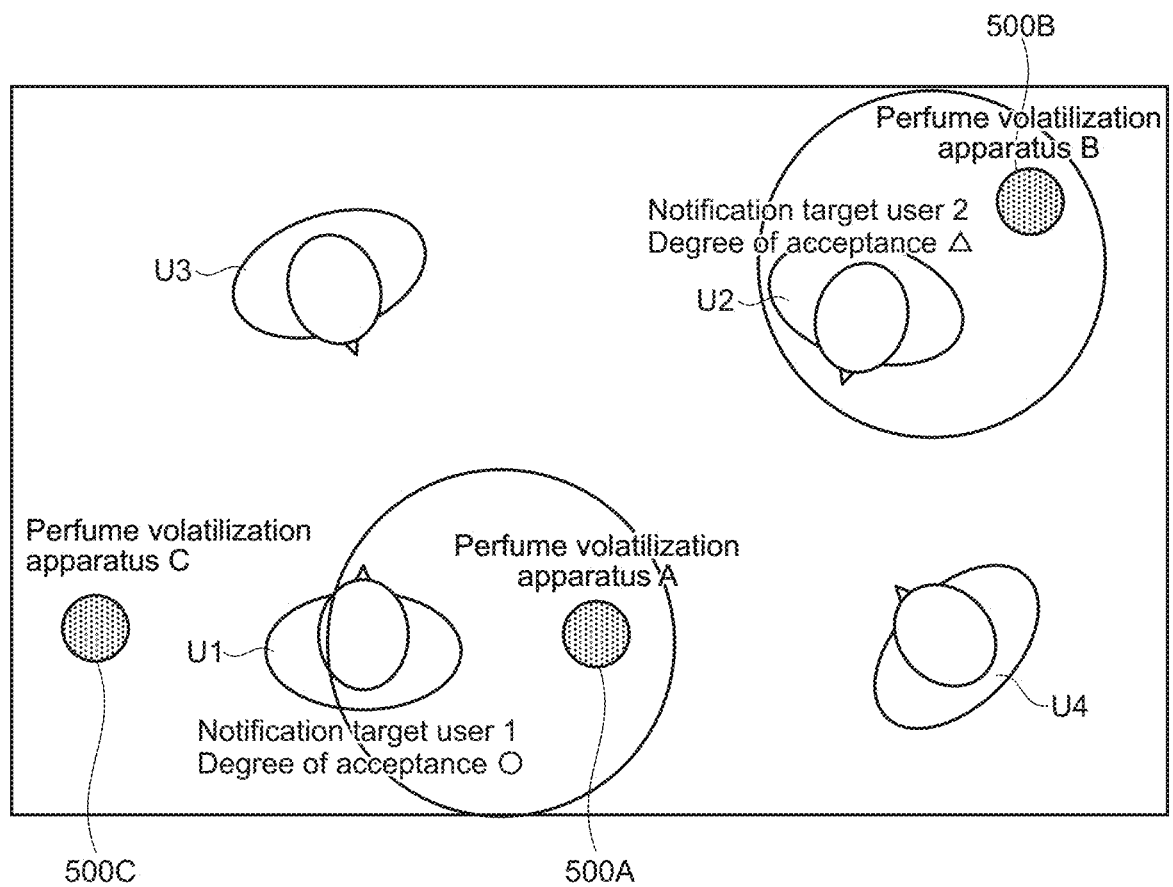
FIG. 11 A diagram for describing determination processing as to whether or not presentation of a scent to a plurality of users is possible in the perfume volatilization system according to the first embodiment.

Further, as shown in FIG. 11, in a case where there are a plurality of target users (users U1, U2, U3, and U4) and a plurality of perfume volatilization apparatuses 500 (perfume volatilization apparatuses A, B, and C), the CPU 11 selects a combination such that the target users are included in the volatilization area of each perfume volatilization apparatus and the non-target users are exclusive.

In the example of the figure, the perfume volatilization apparatus A is selected as the target user U1 and the perfume volatilization apparatus B is selected as the target user U2. Since the degree of acceptance of the target user U2 is Δ, the perfume volatilization apparatus B restricts the output of the perfume.

Further, as in the example of FIG. 10B, in a case where the selective presentation of the scent to the target user U1 is not possible (NO in Step 65), the CPU 11 evaluates the degree of acceptance of the scent of the non-target user (Step 69). This evaluation method is similar to the processing in the case of the target user shown in FIG. 8.

In a case where it is determined that the non-target user has a high degree of acceptance for the scent (Yes), the CPU 11 causes the target user and the non-target user to output the scent from the perfume volatilization apparatus 500.

In a case where it is determined that the degree of acceptance of the non-target user for the scent is low (No), it is determined whether or not the target user can wait for the presentation of the content to the target user presentation of the content to the target user (Step 68). This determination processing and the subsequent processing according to the determination are similar to those described above.

As described above, in accordance with this embodiment, it is possible to control the output of the scent for each of the plurality of users existing in the same space.

Second Embodiment

Next, a second embodiment of the present technology will be described. In this embodiment, portions having functions and configurations similar to those of the first embodiment will be denoted by the same reference signs, and overlapping descriptions will be omitted or simplified.

In the above-mentioned embodiment, the information processing apparatus 100 may use another modal instead of the perfume volatilization apparatus 500 or may use a combination of the perfume volatilization apparatus 500 and another modal in a case where the output of the scent is limited or a case where the output of the scent needs to be gotten by the target user.

Figure 12:
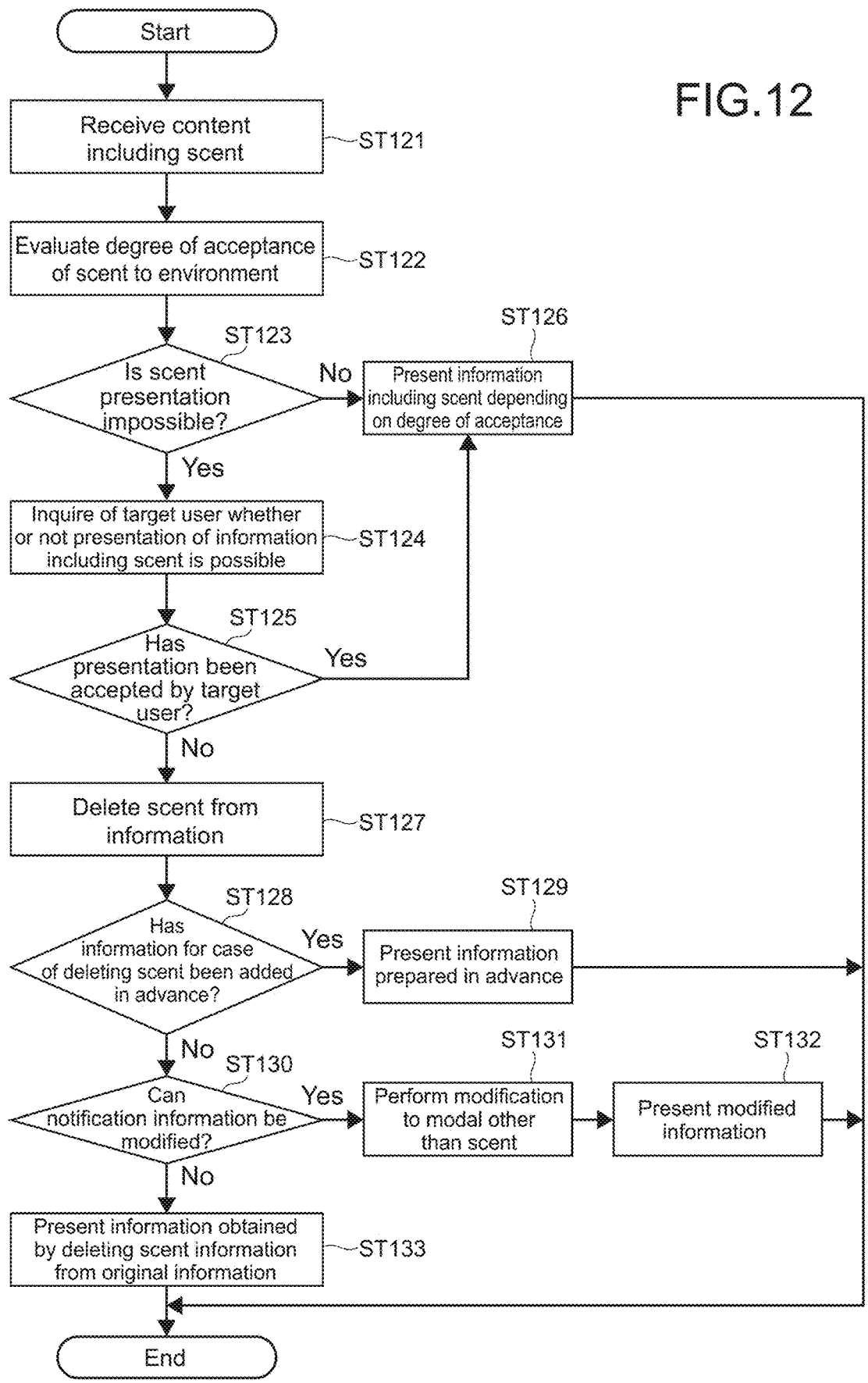
FIG. 12 A flowchart showing a flow of perfume volatilization processing in a perfume volatilization system according to a second embodiment of the present technology.

FIG. 12 is a flowchart showing a flow of content output processing using the other modal.

As shown in the figure, the CPU 11 receives the content including the scent as described in FIG. 6 above (Step 121) and evaluates the degree of acceptance of the scent to the environment (Step 122).

In a case where as a result of the above evaluation, it is determined that the presentation of the scent to the target user is acceptable (NO in Step 123), the CPU 11 presents the content including the scent in accordance with the degree of acceptance of the target user (and the non-target user) for the scent in a manner similar to that of the above-mentioned first embodiment (Step 126).

On the other hand, in a case where as a result of the above evaluation, it is determined that the presentation of the scent to the target user is unacceptable (Yes in Step 123), the CPU 11 inquires of the target user whether or not the presentation of the content including the scent is possible (Step 124).

Figure 13A:
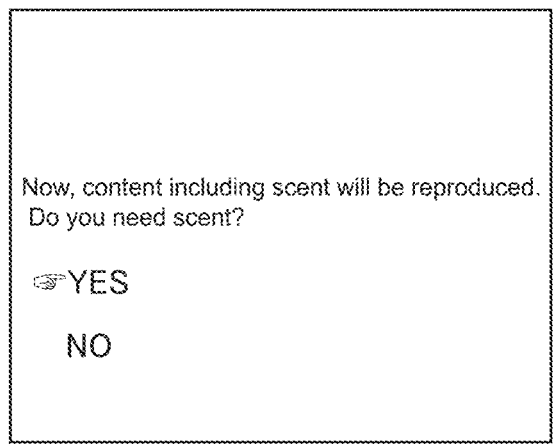
FIGS. 13A, 13B, 13C, and 13D Diagrams showing a display example of content in a case where a scent has been deleted from the content in the perfume volatilization system according to the second embodiment.
Figure 13B:
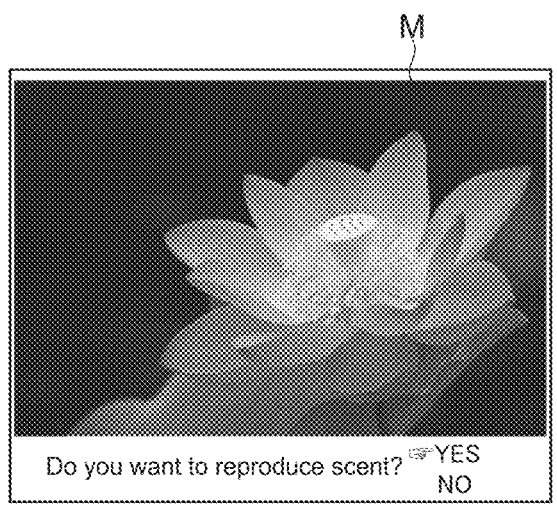

That is, as shown in FIG. 13A, the CPU 11 causes, for example, the video display apparatus 300 to output the fact that the content to be presented includes the scent and option information for inquiring of the user whether or not to accept the output of the scent. The CPU 11 makes the target user explicitly choose whether or not to accept the scent, to thereby allow the target user to be care about the surrounding users.

Alternatively, as shown in B of the figure, the CPU 11 may output information (e.g., video M) other than the scent included in the content and then select whether or not to output the scent.

Referring back to FIG. 12, in a case of receiving the selection to accept the presentation of the scent from the target user (Yes in Step 125), the CPU 11 presents the content including the scent in accordance with the degree of acceptance of the target user (and the non-target user) for the scent in a manner similar to that of the above-mentioned first embodiment (Step 126).

On the other hand, in a case of receiving the selection not to accept the presentation of the scent from the target user (No in Step 125), the CPU 11 deletes the information regarding the scent from the content including the scent (Step 127).

Subsequently, the CPU 11 determines whether or not the information used in a case where the information regarding the scent is deleted has been added to the content in advance (Step 128).

In a case where it is determined that the information used at the time of the deletion is added (Yes), the CPU 11 presents the information to the target user (Step 129).

For example, in a case where the received content includes a video of a flower field and information regarding a scent and the information regarding the scent is deleted, the CPU 11 may present audio information indicating the sound of the wind blowing through the flower field in accordance with a preset setting for the content and may further insert a video recalling the scent (e.g., video in which someone smells). Alternatively, in a case where the information included in the content is only the information regarding the scent and the information regarding the scent is deleted, the CPU 11 may cause a video recalling the scent to be output instead.

Figure 13C:
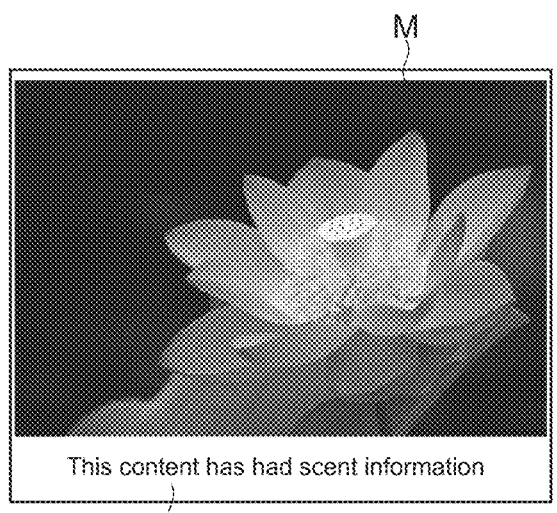
Figure 13D:
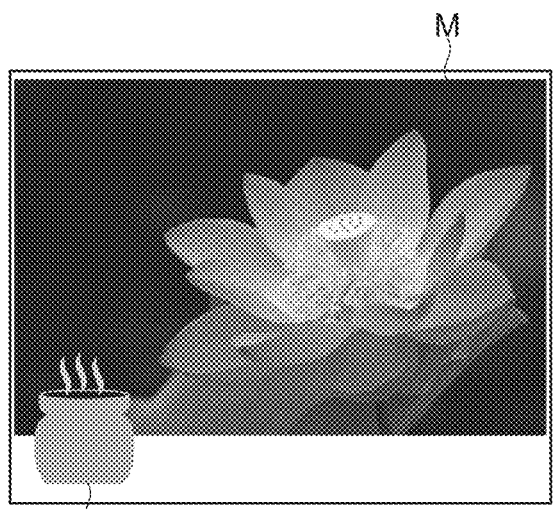

Alternatively, in a case where the information regarding the scent has been deleted, the CPU 11 may also indicate in a text T or an icon I with other information (e.g., video M) included in the content that the content had included the information regarding the scent as shown in FIGS. 13C and 13D.

On the other hand, in a case where it is determined that the information in a case where the information regarding the scent is deleted has not been added to the content (No in Step 128), the CPU 11 determines whether or not the transformation such as emphasis on the other information included in the content is possible (Step 130).

For example, in a case where the information regarding the scent is deleted from the content including an image showing a painting and information regarding a scent, it is undesirable to add an effector to the painting. Also, in a case where the video itself has a message like a commercial message (CM), it is undesirable to modify it. Therefore, in such a case, for example, the CPU 11 determines that the transformation is impossible (No), and causes the output unit O to output information, which is obtained by deleting the information regarding the scent from the original content, to the target user (Step 133).

On the other hand, in a case where it is determined that the other information can be modified (Yes), the CPU 11 modifies the information other than the scent (Step 131) and outputs the modified information from the output unit O to the target user (Step 132).

As an exemplary modification, it is conceivable to add a video and audio recalling the scent in a case where the original content includes only the information regarding the scent and to add a new sound effect in a case where the original content includes the information regarding the scent and the video.

The above example is the example of processing of the other modal in a case where the information regarding the scent is deleted, though it is also conceivable to use the other modal with the scent.

Figure 14A:
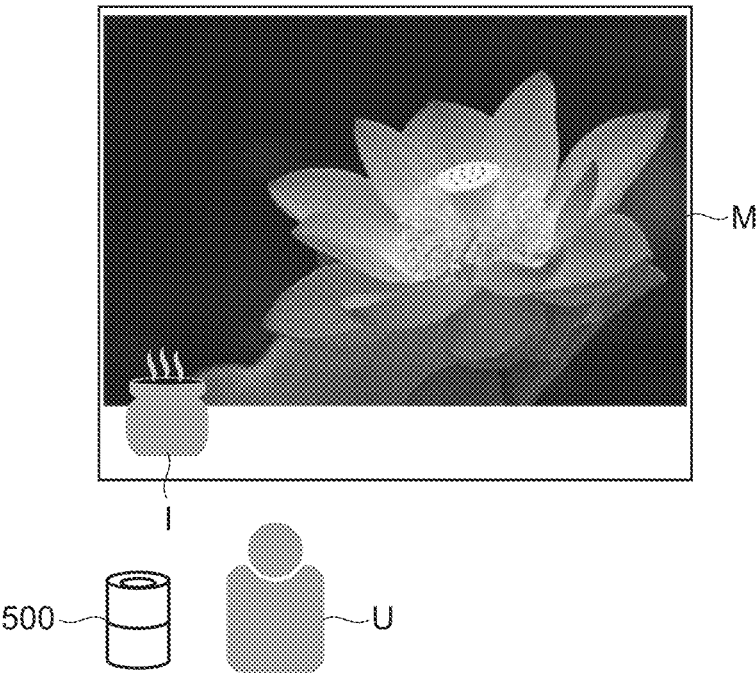
FIGS. 14A and 14B Diagrams showing a display example of the content in a case where the scent has been deleted from the content in the perfume volatilization system according to the second embodiment.
Figure 14B:
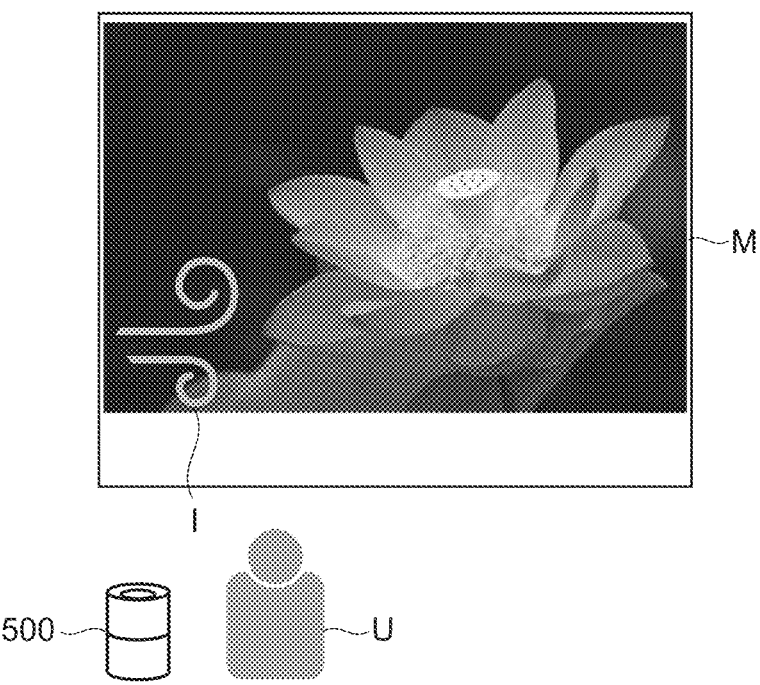

For example, when reproducing content including an image M and information regarding a scent as shown in FIG. 14A, the CPU 11 may cause the output unit O to display the icon I with the image M and cause the display position of the icon I to correspond to a direction of the perfume volatilization apparatus 500 that outputs the scent to the target user as viewed from the user. Accordingly, the target user can get the direction in which the scent is generated.

Alternatively, as shown in B of the figure, the CPU 11 may notify of the target user by displaying the flow path of the scent of the wind or the like as the icon I or the like.

Alternatively, the CPU 11 may present the scent information after the user's attention is drawn to the information presentation by first reproducing the information using a modal easy for the user to recognize by the sense of vision (video display apparatus 300), the sense of hearing (audio output apparatus 400), or the like such the target user can efficiently get the scent when the scent is output.

For example, in a case of presenting an image of a flower and its scent, the CPU 11 may present the image of the flower in advance, and present the scent through the perfume volatilization apparatus 500 after it is confirmed via the detection unit 200 that the target user has visually recognized the image of the flower, to thereby improve the easiness of recognition of the target user. Alternatively, the CPU 11 may cause its status to be displayed as an icon or the like in the video at any time while the scent is being output.

Alternatively, in a case where the content includes only the scent information, the CPU 11 may present a ring tone or the like in advance at the time of receiving the content to call the user's attention, for example.

Alternatively, in order to further improve the user's perception of the scent, the CPU 11 may cause the perfume volatilization apparatus 500 to explicitly eject smog or the like or may cause the perfume volatilization apparatus 500 to light up.

Modified Examples

The present technology is not limited to the above-mentioned embodiments and can be variously modified without departing from the gist of the present technology.

In the above-mentioned embodiments, in a case of consecutively presenting a plurality of scents, the CPU 11 may control the perfume volatilization apparatus 500 in advance to control the presentation of the scents. For example, as described above in the first embodiment, the time required for the scent to arrive at the target user may be calculated and the reproduction time of the content may be gotten, both may be compared, volatilization of the perfume from the perfume volatilization apparatus 500 may be started before the video or the like of the content to be presented is output, and the output timing of the perfume may be controlled such that the scent arrives at the user at the start of the content.

Figure 15:
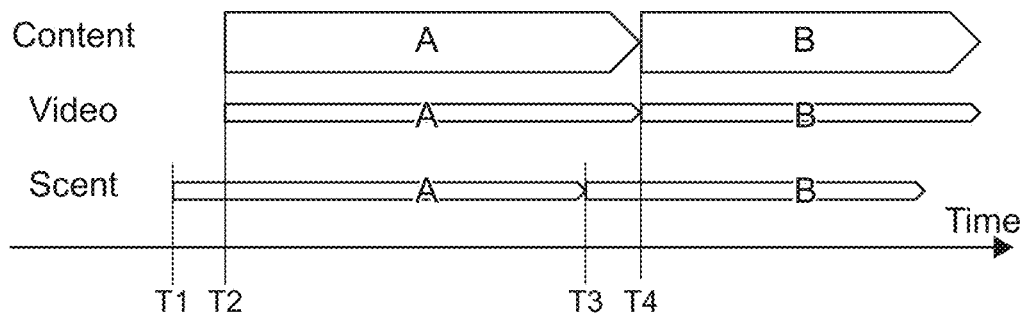
FIG. 15 A diagram for describing a presentation timing of a scent according to content in a modified example of the perfume volatilization system.

Specifically, as shown in FIG. 15, the CPU 11 controls an output timing T1 of a scent A such that the corresponding scent arrives at the user at a reproduction start time T2 of content A. Further, the CPU 11 controls an output timing T3 of the scent B (and an output stop timing of the scent A) such that the corresponding scent arrives at the user at a reproduction start time T4 of content B.

Figure 16:
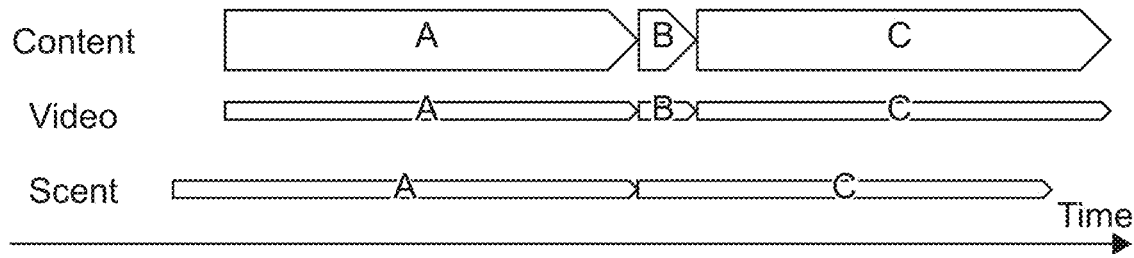
FIG. 16 A diagram for describing a presentation timing of a scent according to content in a modified example of the perfume volatilization system.

Alternatively, when consecutively presenting scents, the CPU 11 may control the perfume volatilization apparatus 500 not to present the scent of the content B in a case where the time of the content B is shorter than the time required for volatilization of the perfume, for example, in a case where the relatively short content B is inserted between the content A and content C as shown in FIG. 16 (e.g., CM in television).

That is, the CPU 11 compares the reproduction time of the content B with the arrival time at the user from the start of outputting the corresponding scent, and stops the output of the scent in a case where the reproduction time is shorter than the arrival time.

In the above-mentioned embodiments, in a case where it is determined from the sensing information of the detection unit 200 that there is a possibility that a plurality of scents to be output to the respective users is mixed, the CPU 11 may output the plurality of scents at predetermined time intervals or may output another of scents at a timing when it is determined on the basis of the sensing information that the intensity of output one of the scents becomes equal to or lower than a threshold.

In the above-mentioned embodiments, the CPU 11 may set a mode on which the presentation of the scent is turned off in a case where the presence of a third party such as a customer in the space is detected, and may allow the presentation using the scent in a case where the user performs an explicit operation.

In the above-mentioned embodiments, in a case where the perfume volatilization apparatus 500 is wearable, the CPU 11 may present the scent not considering the target user but only considering the non-target user because the scent is directly output to the wearing user.

In the above-mentioned embodiments, in a case where the face (nose) orientation of the target user is detected by a camera or the like and it is determined that the face (nose) of the target user does not face the perfume volatilization apparatus 500, the CPU 11 may alert the user to turn toward the perfume volatilization apparatus 500 (e.g., output sound or light) or may output the scent at a timing when it is detected that the user has turned toward the volatilization apparatus.

[Others]

The present technology can also take configurations as follows.

(1) An information processing apparatus, including:

an input unit into which sensing information sensed in a predetermined space is input; and a control unit that controls, in accordance with a result obtained by analyzing states or attributes of a plurality of users existing in the space on a basis of the sensing information, output of a scent from the scent output apparatus to each of the users for each user.

(2) The information processing apparatus according to (1), in which the control unit changes kind and intensity of the scent in accordance with the state or the attribute of the user.

(3) The information processing apparatus according to (2), in which the control unit determines a degree of acceptance of each user for a plurality of different scents in accordance with the state or the attribute of each of the users and determines the kind or the intensity of the scent to be output to each of the users and whether to output to each user in accordance with the degree of acceptance.

(4) The information processing apparatus according to any of (1) to (3), in which the scent output apparatus includes a plurality of scent output apparatuses arranged at different positions in the space, and the control unit determines, on a basis of the sensing information, a scent output apparatus of the plurality of scent output apparatuses, which has a shortest arrival time of the scent at the user, as an apparatus for outputting the scent to each of the users.

(5) The information processing apparatus according to (4), in which in a case where a distance between at least two scent output apparatuses of the plurality of scent output apparatuses and one user of the plurality of users is equal or approximately equal, the control unit determines, on a basis of face orientation information of the user obtained from the sensing information, a scent output apparatus of the two scent output apparatuses, which is closer in a face orientation of the user, as an apparatus for outputting the scent.

(6) The information processing apparatus according to (4) or (5), in which the control unit determines the arrival time on a basis of wind direction information between each of the users and each of the scent output apparatuses, the wind direction information being obtained from the sensing information.

(7) The information processing apparatus according to any of (1) to (6), in which the control unit outputs a video or audio associated with the scent before or during output of the scent to each of the users.

(8) The information processing apparatus according to any of (1) to (7), in which the control unit outputs notification information for notifying of a direction in which the scent is generated before or during output of the scent to each of the users.

(9) The information processing apparatus according to any of (1) to (8), in which in a case where content associated with the scent is input by the input unit, the control unit determines a user of the plurality of users, who is an output target of the scent, on a basis of information included in the content and controls the output of the scent for each of a user who is the output target and a user who is not the output target.

(10) The information processing apparatus according to (9), in which the control unit outputs information indicating presence of the scent together with the content on a basis of the state or the attribute of each user in a case where it is determined that output of the scent associated with the content is impossible.

(11) The information processing apparatus according to (9) or (10), in which the content includes first content associated with a first scent and second content associated with a second scent, which are consecutively reproducible, and the control unit controls an output timing of the first scent such that the first scent arrives at each of the users at a time of reproduction start of the first content and controls an output timing of the second scent and an output stop timing of the first scent such that the second scent arrives at each of the users at a time of reproduction start of the second content.

(12) The information processing apparatus according to (11), in which the control unit compares a reproduction time of the first content or the second content with an arrival time at each of the users from output of the first scent or the second scent, and stops the output of the first scent or the second scent in a case where the reproduction time is shorter than the arrival time.

(13) The information processing apparatus according to any of (1) to (12), in which in a case where it is determined that there is a possibility that a plurality of scents to be output to the respective users is mixed on a basis of the sensing information, the control unit outputs the plurality of scents at predetermined time intervals or outputs another one of the scents at a timing when it is determined that intensity of output one of the scents becomes equal to or lower than a threshold on a basis of the sensing information.

(14) An information processing method, including:

receiving input of sensing information sensed in a predetermined space; and controls, in accordance with a result obtained by analyzing states or attributes of a plurality of users existing in the space on a basis of the sensing information, output of a scent from a scent output apparatus to each of the users for each user.

(15) A program that causes an information processing apparatus to execute:

a step of receiving input of sensing information sensed in a predetermined space; and a step of controlling, in accordance with a result obtained by analyzing states or attributes of a plurality of users existing in the space on a basis of the sensing information, output of a scent from a scent output apparatus to each of the users for each user.

REFERENCE SIGNS LIST

11 CPU
18 input apparatus 19 output apparatus
20 storage apparatus
26 image pickup apparatus
23 communication apparatus
100 information processing apparatus
200 detector
300 video display apparatus
400 audio output apparatus
500 perfume volatilization apparatus

The invention claimed is:

1. An information processing apparatus, comprising:
a plurality of sensors configured to acquire sensing information corresponding to a specific space; and
a central processing unit (CPU) configured to:
analyze at least one of a state or an attribute of each user of a plurality of users that exists in the specific space, wherein the analysis of the at least one of the state or the attribute is based on the sensing information;
receive content associated with a specific scent, wherein the content includes first information;
determines, based on the first information of the content, a first user of the plurality of users as an output target of the specific scent;
control output of the specific scent from at least one scent output apparatus of a plurality of scent output apparatuses to each of the first user and a second user of the plurality of users, wherein the second for each user is not the output target; and
output the content with second information that indicates presence of the specific scent, based on the at least one of the state or the attribute, in a case where the output of the specific scent associated with the content is impossible.

2. The information processing apparatus according to claim 1, wherein
the CPU is further configured to change a kind and an intensity of the specific scent based on the at least one of the state or the attribute of each user of the plurality of users.

3. The information processing apparatus according to claim 2, wherein the CPU is further configured to:
determine, based on the at least one of the state or the attribute of each user of the plurality of users, a degree of acceptance of each user of the plurality of users for a plurality of different scents, wherein the plurality of different scents includes the specific scent;
determine, based on the determined degree of acceptance, at least one of the kind or the intensity of the specific scent; and
determine to output, based on the determined degree of acceptance and the determination of the at least one of the kind or the intensity of the specific scent, the specific scent to each user of the plurality of users.

4. The information processing apparatus according to claim 1, wherein
each of the plurality of scent output apparatuses exists at different positions in the specific space,
the CPU is further configured to determine, based on the sensing information, a scent output apparatus as an apparatus to output the specific scent to each user of the plurality of users,
the plurality of scent output apparatuses includes the scent output apparatus, and
the determined scent output apparatus has a shortest arrival time of the specific scent to a specific user of the plurality of users.

5. The information processing apparatus according to claim 4, wherein the CPU is further configured to:
determine face orientation information of the specific user based on the sensing information; and
select, based on the determined face orientation information and a determination that a distance between at least two scent output apparatuses and the specific user is one of equal or approximately equal, the scent output apparatus from the at least two scent output apparatuses as an apparatus to output the specific scent, wherein
the selected scent output apparatus is closest to the specific user in a face orientation direction of the specific user, and
the plurality of scent output apparatuses includes the at least two scent output apparatuses.

6. The information processing apparatus according to claim 4, wherein the CPU is further configured to:
acquire, from the sensing information, wind direction information between each user of the plurality of users and each of the plurality of scent output apparatuses; and
determine an arrival time of the specific scent based on the wind direction information between each user of the plurality of users and each of the scent output apparatuses.

7. The information processing apparatus according to claim 1, wherein the CPU is further configured to output, one of before or during the output of the specific scent to each user of the plurality of users, at least one of a video or an audio associated with the specific scent.

8. The information processing apparatus according to claim 1, wherein
the CPU is further configured to output, one of before or during output of the specific scent to each of the plurality of users, notification information to notify a direction to the plurality of users, and
the notified direction corresponds to an output direction of the specific scent.

9. The information processing apparatus according to claim 1, wherein
the content includes first content associated with a first scent and second content associated with a second scent,
the first scent and the second scent which are consecutively reproducible, and
the CPU is further configured to:
control a first output timing of the first scent, wherein
the first scent arrives to each of the plurality of users based on the controlled first output timing, and
the first scent arrives at each of the plurality of users at a reproduction start time of the first content; and
control a second output timing of the second scent and an output stop timing of the first scent, wherein
the second scent arrives at each of the plurality of users based on the controlled second output timing and the controlled output stop timing, and
the second scent arrives at each of the plurality of users at a reproduction start time of the second content.

10. The information processing apparatus according to claim 9, wherein the CPU is further configured to:
compare a reproduction time of one of the first content or the second content with an arrival time of one of the first scent or the second scent at each of the plurality of users; and
stop the output of one of the first scent or the second scent based on a determination that the reproduction time is shorter than the arrival time.

11. The information processing apparatus according to claim 1, wherein
the CPU is further configured to:
determine, based on the sensing information, a possibility that a plurality of scents output to the plurality of users is mixed, wherein the plurality of scents includes the specific scent; and
output, based on the determined possibility, the plurality of scents at specific time intervals, or
the CPU is further configured to:
determine, based on the sensing information, a timing at which an intensity of a first scent is equal to or lower than a threshold, wherein the plurality of scents includes the first scent; and
output a second scent of the plurality of scents at the determined timing.

12. An information processing method, comprising:
receiving input of sensing information corresponding to a specific space;
analyzing at least one of a state or an attribute of each user of a plurality of users existing in the space, wherein the analyzing of the at least one of the state or the attribute is based on the sensing information;
receiving content associated with a scent, wherein the content includes first information;
determining, based on the first information of the content, a first user of the plurality of users as an output target of the scent;
controlling output of the scent from at least one scent output apparatus of a plurality of scent output apparatuses to each of the first user and a second user of the plurality of users, wherein the second user is not the output target; and
outputting the content with second information that indicates presence of the scent, based on the at least one of the state or the attribute, in a case where the output of the scent associated with the content is impossible.

13. A program that causes an information processing apparatus to execute non-transitory computer-readable medium having stored thereon, computer-executable instructions which, when executed by a central processing unit (CPU), cause the CPU to execute operations, the operations comprising:
receiving input of sensing information corresponding to a predetermined space;
analyzing at least one of a state or an attribute of each user of a plurality of users existing in the space, wherein the analyzing of the at least one of the state or the attribute is based on the sensing information;
receiving content associated with a scent, wherein the content includes first information;
determining, based on the first information of the content, a first user of the plurality of users as an output target of the scent;
controlling output of the scent from at least one scent output apparatus of a plurality of scent output apparatuses to each of the first user and a second user of the plurality of users, wherein the second user is not the output target; and
outputting the content with second information that indicates presence of the scent, based on the at least one of the state or the attribute, in a case where the output of the scent associated with the content is impossible.

* * * * *